US006894197B2

(12) United States Patent
Mimura et al.

(10) Patent No.: US 6,894,197 B2
(45) Date of Patent: May 17, 2005

(54) PROCESS FOR PRODUCING FLUORINATED ALCOHOL

(75) Inventors: Hideyuki Mimura, Yamaguchi (JP); Kosuke Kawada, Yamaguchi (JP); Shoji Arai, Yamaguchi (JP)

(73) Assignee: Tosoh F-Tech, Inc., Yamaguchi (JP)

( * ) Notice: Subject to any disclaimer, the term of this patent is extended or adjusted under 35 U.S.C. 154(b) by 0 days.

(21) Appl. No.: 10/476,540

(22) PCT Filed: Jul. 1, 2002

(86) PCT No.: PCT/JP02/06632

§ 371 (c)(1), (2), (4) Date: Mar. 1, 2004

(87) PCT Pub. No.: WO03/004446

PCT Pub. Date: Jan. 16, 2003

(65) Prior Publication Data

US 2004/0152926 A1 Aug. 5, 2004

(30) Foreign Application Priority Data

Jul. 2, 2001 (JP) ....................................... 2001-200338

(51) Int. Cl.[7] ......................... C07C 31/34; C07C 31/38; C07C 31/42; C07C 31/44

(52) U.S. Cl. ........................................ 568/842; 570/142

(58) Field of Search ........................... 568/842; 570/142

(56) References Cited

U.S. PATENT DOCUMENTS

| | | | | |
|---|---|---|---|---|
| 4,489,211 A | * 12/1984 | Ogura et al. | ................ | 568/842 |
| 4,748,282 A | 5/1988 | Bargigia et al. | | |
| 5,264,637 A | 11/1993 | Yoshida et al. | | |
| 6,111,130 A | * 8/2000 | Van Der Puy | .............. | 560/111 |

FOREIGN PATENT DOCUMENTS

| | | |
|---|---|---|
| DE | 33 04 779 | 9/1983 |
| EP | 0 247 614 | 5/1987 |
| EP | 0 371 399 | 11/1989 |
| GB | 2 117 376 | 10/1983 |
| IT | 1190116 | 2/1988 |
| JP | 58-134043 | 8/1983 |
| JP | 58-140031 | 8/1983 |
| JP | 62-273925 | 11/1987 |
| JP | 63-22040 | 1/1988 |
| JP | 2-142740 | 5/1990 |
| JP | 2-142741 | 5/1990 |
| NL | 8300551 | 2/1983 |

OTHER PUBLICATIONS

Albert L. Henne and Earl G. Dewitt, Difluoromalonic Derivatives from Difluoropentane, J. Am. Chem. Soc. 70, 1548–1550 (1948).

R. Cloux, E. sz. Kovats, "Radical Addition of 2,2,2–Trifluroethyl Iodide to Terminal Alkenes," Synthesis, 409, Apr. 1992.

* cited by examiner

*Primary Examiner*—Elvis O. Price
(74) *Attorney, Agent, or Firm*—Wenderoth, Lind & Ponack, L.L.P.

(57) ABSTRACT

A method for producing fluorinated alcohols from fluorinated alkyl halides can produce fluorinated alcohols at high product yield and at high selectivity in a single-step reaction. The method eliminates the need to use heavy metals and other toxic compounds that are difficult to handle or process.

Specifically, the method produces a fluorinated alcohol represented by the following general formula (2):

$$Rf(A)OH \quad (2)$$

wherein Rf represents a perfluoroalkyl group having 1 to 10 carbon atoms; and A represents a straight-chained or branched saturated hydrocarbon group having 3 to 10 carbon atoms. The method is characterized in that it allows a fluorinated alkyl halide represented by the following general formula (1) to react with an alkali metal salt of 4-hydroxybutyrate in a gamma-butyrolactone solvent:

$$Rf(A)X \quad (1)$$

wherein Rf and A are as defined above; and X represents a halogen atom.

5 Claims, No Drawings

PROCESS FOR PRODUCING FLUORINATED ALCOHOL

FIELD OF THE INVENTION

The present invention relates to a method for producing fluorinated alcohols through hydrolysis of fluorinated alkyl halides.

TECHNICAL FIELD

Fluorinated alcohols are highly useful compounds suitable for use as a material for water/oil repellants and surfactants, or as an intermediate for the production of pharmaceutical agents. Reactions for producing alcohols through hydrolysis of alkyl halides are widely known processes. These reactions, however, are often associated with undesirable side reactions such as dehydrohalogenation and etherification that can result in a reduced yield of the alcohols. When this type of reaction is applied to fluorinated alkyl halides to hydrolyze them, the side reactions tend to become significant and the resulting by-products, which often have a boiling point close to that of the desired fluorinated alcohol or can form an azeotrope with the fluorinated alcohol, make the isolation and purification of the desired product difficult. Also, when the fluorinated alcohols are intended for use as an intermediate for the production of pharmaceutical agents, these impurities may not be acceptable even in trace amounts. For these reasons, it is important to minimize these side reactions.

One common method for hydrolyzing alkyl halides involves the use of sodium acetate in an acetic acid solvent (*Organic Synthesis*, III 650 (1955)). In this process, the resultant ester intermediates must be separated from the acetic acid solvent and must be hydrolyzed in a potassium hydroxide solution. This makes the process undesirably complicated. A method that allows the synthesis of fluorinated alcohols from fluorinated alkyl halides at high selectivity is disclosed in Japanese Patent Laid-Open Publication No. Sho 63-22040. This technique is characterized in that it makes use of transitional metal ions as a catalyst. The reaction is a single-step process, yet it requires the use of heavy metals. Thus, not only does the reaction require a separate process to process the heavy metals, but also it produces heavy metal compounds that are difficult to be disposed of.

DISCLOSURE OF THE INVENTION

Accordingly, it is an objective of the present invention to provide a method for producing fluorinated alcohols that can overcome the aforementioned drawbacks of prior art. This method minimizes undesirable side reactions and is a single-step reaction that ensures high product yield as well as high selectivity of the desired fluorinated alcohol. The method also allows for the production of fluorinated alcohols from fluorinated alkyl halides without using heavy metals and other toxic compounds that are difficult to handle or process.

During the course of studies to find ways to solve the above-described problems, the present inventors have found that by allowing fluorinated alkyl halides to undergo reaction in the presence of 4-hydroxybutyrate with the help of a specific solvent, fluorinated alcohols can be obtained at high yield and at high selectivity. This discovery encouraged the present inventors to devise the present invention.

Thus, a first invention concerns a method for producing a fluorinated alcohol represented by the following general formula (2):

$$Rf(A)OH \qquad (2)$$

wherein Rf represents a perfluoroalkyl group having 1 to 10 carbon atoms; and A represents a straight-chained or branched saturated hydrocarbon group having 3 to 10 carbon atoms, the method comprising the step of:

allowing a fluorinated alkyl halide represented by the following general formula (1) to react with an alkali metal salt of 4-hydroxybutyrate in a gamma-butyrolactone solvent:

$$Rf(A)X \qquad (1)$$

wherein Rf and A are as defined above; and X represents a halogen atom.

A second invention is the method of the first invention wherein the reaction is allowed to proceed at a temperature of 120° C. or below until the amount of the remaining fluorinated alkyl halide becomes 10% or less and is subsequently carried out at a temperature of 120° C. or above.

A third invention concerns the first or the second invention wherein the alkali metal salt of 4-hydroxybutyrate is a potassium salt of 4-hydroxybutyrate.

A fourth invention is any one of the first to the third invention wherein the fluorinated alkyl halide is 4,4,4-trifluorobutylhalide and the fluorinated alcohol is 4,4,4-trifluorobutanol.

A fifth invention concerns any one of the first to the fourth invention wherein the resulting fluorinated alcohol is distilled out to facilitate the conversion of 4-hydroxybutyric acid ester, an intermediate present in the reaction mixture, into the fluorinated alcohol and the gamma-butyrolactone.

BEST MODE FOR CARRYING OUT THE INVENTION

The present invention will now be described in further detail.

Fluorinated alkyl halides for use in the present invention are compounds represented by the above-described general formula (1), wherein X represents a halogen atom selected from the group consisting of Cl, Br, and I. Examples of such fluorinated alkyl halides include 4,4,4-trifluorobutylchloride, 4,4,4-trifluorobutylbromide, 4,4,4-trifluorobutyliodide, 5,5,5,4,4-pentafluoropentyliodide, 1-methyl-4,4,4-trifluorobutyliodide, and 10,10,10,9,9,8,8,7,7-nonafluorodecylchloride.

Fluorinated alcohols obtained through the method of the present invention are compounds represented by the above-described general formula (2). Examples include 4,4,4-trifluorobutanol, 5,5,5,4,4-pentafluoropentanol, 1-methyl-4,4,4-trifluorobutanol, and 10,10,10,9,9,8,8,7,7-nonafluorodecanol.

According to the present invention, alkali metal salts of 4-hydroxybutyric acid are used to serve as a reactant. The alkali metal salts of 4-hydroxybutyric acid are generally synthesized by first adding an aqueous solution of an alkali metal hydroxide to gamma-butyrolactone and subsequently distilling water out of the solution. It may also be synthesized by adding an alkali metal hydroxide to gamma-butyrolactone. If available, the commercially available products may also be used. Examples of the alkali metal salt of 4-hydroxybutyric acid include lithium 4-hydroxybutyrate, sodium 4-hydroxybutyrate, potassium 4-hydroxybutyrate, rubidium 4-hydroxybutyrate, and cesium 4-hydroxybutyrate. Of these, potassium 4-hydroxybutyrate is preferred because of the readiness of its synthesis and its availability and in terms of product yield. The amount of the alkali metal salt of 4-hydroxybutyric acid is typically in the range of 0.25 to 4 molar equivalents and preferably in the range of 0.5 to 2 molar equivalents of the amount of the fluorinated alkyl halide. If the amount of the alkali metal salt is less than 0.25 molar equivalents of the fluorinated alkyl halide, some of the fluorinated alkyl halide will remain unreacted, making the collection of the alkyl halide difficult. In contrast, the alkali metal salt, when contained in an amount larger than 4 molar equivalents of the fluorinated alkyl halide, can give rise to the unwanted side reactions.

The reaction solvent for use in the present invention is gamma-butyrolactone, which may be used in conjunction with water or one or more organic solvents selected from methanol, acetone, dioxane, acetonitrile, N,N-dimethylformamide, N-methylpyrrolidone, N,N-dimethylindazolinone, and dimethylsulfoxide. The amount by weight of the solvent is typically in the range of 0.5 to 20 times, and preferably in the range of 1 to 10 times the weight of the fluorinated alkyl halide. The solvent, when used in an amount by weight of less than 0.5 times the amount of the fluorinated alkyl halide, may result in an insufficient yield, whereas the solvent used in an amount by weight of more than 20 times the amount of fluorinated alkyl halide makes collection of the solvent difficult.

In the present invention, the reaction temperature is generally in the range of 50 to 220° C. The temperature of 50° C. or below may result in too slow a reaction rate, whereas the temperature above 220° C. may give rise to the generation of unwanted by-products.

The reaction temperature may initially be kept at 50 to 120° C. until the remaining amount of the fluorinated alkyl halide is decreased to 10% or less of the initial amount and subsequently kept at 120 to 220° C. In this manner, generation of the fluorinated alkyl ether by-products is significantly decreased and thus, the present invention can be carried out in a more suitable manner.

In the present invention, it is desirable that the reaction mixture be thoroughly mixed. While the rate of stirring may vary depending upon the shape of the reactor and the vanes for stirring and other factors, it is generally in the range of 300 to 2000 rpm. The reaction time is typically in the range of 1 to 48 hours while the reaction may be carried out over any length of time. Preferably, the reaction of the present invention is carried out under inert gas atmosphere such as nitrogen, argon, and carbon dioxide. While the reaction is generally carried out under atmospheric pressure, it may be carried out, if necessary, under increased or reduced pressure.

The fluorinated alcohol product can be readily purified using distillation or other known separation techniques. Without wishing to be bound by a particular theory, it is believed that, in hydrolysis in accordance with the present invention, a fluorinated alkyl halide (1) reacts with an alkali metal salt of 4-hydroxybutyric acid (3) to form a 4-hydroxybutyric acid ester intermediate (4). It is believed that this ester intermediate, remaining in the reaction mixture, is in equilibrium with the fluorinated alcohol and the gamma-butyrolactone, so that as the fluorinated alcohol is removed by distillation or other suitable separation techniques, the remaining ester intermediate (4) is converted to fluorinated alcohol (2) and gamma-butyrolactone (5) and is eventually eliminated. As a result, the yield of the fluorinated alcohol (2) is increased.

(Chemical equation 1)

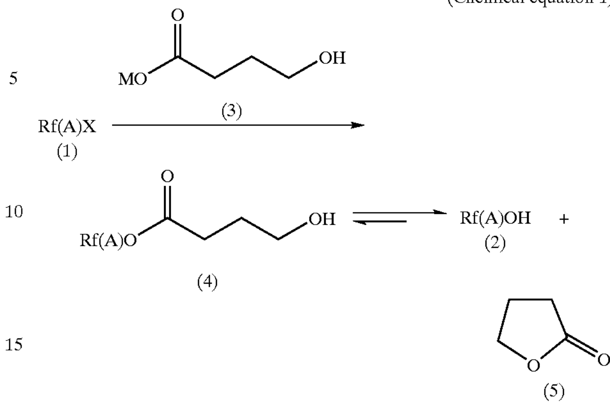

The present invention will now be described in detail with reference to examples, which are intended to be only illustrative and do not limit the scope of the invention in any way.

EXAMPLE 1

250 g gamma-butyrolactone, 62.5 g (440 mmol) potassium 4-hydroxybutyrate, and 95.2 g (400 mmol) 4,4,4-trifluorobutyliodide were placed in a 500 ml four-necked flask equipped with a stirrer, a reflux cooler, and a thermometer. By heating, the mixture was maintained at 75° C. for 5 hours while being stirred. At this point, it was determined by a gas chromatography that 98.6% of the 4,4,4-trifluorobutyliodide had been converted. Subsequently, the temperature was raised to 140° C. and the reaction was allowed to continue for another 2 hours. Upon completion of the reaction, the mixture was again analyzed by a gas chromatography. The results of the analysis revealed that 4,4,4-trifluorobutyliodide was converted at 100% conversion rate, and the selectivity for 4,4,4-trifluorobutanol, trifluorobutyl 4-hydroxybutyrate, and 4,4,4-trifluoro-1-butene were 86.5%, 13.3%, and 0.2%, respectively.

The reaction mixture was then subjected to distillation: it was transferred to a 500 ml flask equipped with a Claisen connector tube and a Liebig's cooling tube, and was distilled at 120 to 140° C. under a pressure of 20 to 6 kPa while the degree of vacuum was increased over a 3-hour period. As a result, 70.4 g distillate was collected containing 49.2 g (96.0% yield) of 4,4,4-trifluorobutanol. The gas chromatography analysis performed on the solution remaining in the flask indicated that it contained 0.8% trifluorobutyl 4-hydroxybutyrate.

EXAMPLE 2

In a 500 ml four-necked flask equipped with a stirrer, a thermometer, a Claisen connector tube, and a Liebig's cooling tube, 250 g gamma-butyrolactone was placed along with 51.4 g (440 mmol) of 48% aqueous solution of potassium hydroxide. To distill water, the mixture was heated to an inner temperature of 140° C. at a pressure of 20 kPa while being stirred. The mixture was then allowed to cool to approximately 50° C. and the pressure was brought back to atmospheric pressure. 95.2 g (400 mmol) 4,4,4-trifluorobutyliodide was then added to the mixture and the mixture was heated for 5 hours at 75° C. The results of a gas chromatography analysis indicated that 99.1% of 4,4,4-trifluorobutyliodide had been converted. The reaction temperature was then increased to 140° C. and the reaction was allowed to continue for another 2 hours.

Upon completion of the reaction, the mixture was again analyzed by a gas chromatography. The results of the analysis revealed that 4,4,4-trifluorobutyliodide was converted at 100% conversion rate, and the selectivity for 4,4,4-trifluorobutanol, trifluorobutyl 4-hydroxybutyrate, and 4,4,4-trifluoro-1-butene were 88.3%, 11.4%, and 0.3%, respectively.

EXAMPLE 3

The reaction was carried out in the same manner as in Example 1, except that the reaction was performed for 7 hours at 140° C. A gas chromatography analysis was performed when the temperature reached 140° C. and the results indicated that 85.5% of 4,4,4-trifluorobutyliodide had been converted by then. Upon completion of the reaction, the mixture was again analyzed by a gas chromatography, the results of which revealed that 4,4,4-trifluorobutyliodide was converted at 100% conversion rate, and the selectivity for 4,4,4-trifluorobutanol, trifluorobutyl 4-hydroxybutyrate, 4,4,4-trifluoro-1-butene, and bis(4,4,4-trifluorobutyl)ether were 85.3%, 12.3%, 0.2% and 2.2%, respectively.

EXAMPLE 4

The reaction was carried out in the same manner as in Example 1, except that 55.4 g (440 mmol) sodium 4-hydroxybutyrate was used in place of potassium 4-hydroxybutyrate and the temperature was maintained at 100° C. for 5 hours and subsequently at 140° C. for 2 hours. Upon completion of the reaction, the mixture was analyzed by a gas chromatography. The results of the analysis revealed that 4,4,4-trifluorobutyliodide was converted at 95.2% conversion rate, and the selectivity for 4,4,4-trifluorobutanol, trifluorobutyl 4-hydroxybutyrate, 4,4,4-trifluoro-1-butene, and bis(4,4,4-trifluorobutyl)ether were 84.9%, 12.3%, 0.3% and 2.5%, respectively.

EXAMPLE 5

The reaction was carried out in the same manner as in Example 1, except that 58.6 g (400 mmol) 4,4,4-trifluorobutylchloride was used in place of 4,4,4-trifluorobutyliodide and the temperature was maintained at 100° C. for 5 hours and subsequently at 140° C. for 2 hours. Upon completion of the reaction, the mixture was analyzed by a gas chromatography. The results of the analysis revealed that 4,4,4-trifluorobutylchloride was converted at 98.2% conversion rate, and the selectivity for 4,4,4-trifluorobutanol, trifluorobutyl 4-hydroxybutyrate, and 4,4,4-trifluoro-1-butene were 87.9%, 11.9%, and 0.2%, respectively.

EXAMPLE 6

The reaction was carried out in the same manner as in Example 1, except that 135.4 g (400 mmol) 10,10,10,9,9,8,8,7,7-nonafluorodecylchloride was used in place of 4,4,4-trifluorobutyliodide and the temperature was maintained at 100° C. for 5 hours and subsequently at 140° C. for 2 hours. Upon completion of the reaction, the mixture was analyzed by a gas chromatography. The results of the analysis revealed that 10,10,10,9,9,8,8,7,7-nonafluorodecylchloride was converted at 100% conversion rate, and the selectivity for 10,10,10,9,9,8,8,7,7-nonafluorodecanol, nonafluorodecyl 4-hydroxybutyrate, and 10,10,10,9,9,8,8,7,7-nonafluoro-1-decene were 82.4%, 17.4%, and 0.2%, respectively.

Comparative Example 1

250 g water, 18.9 g (purity 93%, 440 mmol) sodium hydroxide, and 95.2 g (400 mmol) 4,4,4-trifluorobutyliodide were placed in a 500 ml four-necked flask equipped with a stirrer, a reflux cooler, and a thermometer. By heating, the mixture was maintained at 90° C. for 36 hours while being stirred. As the reaction proceeds, generation of gas was observed. Upon completion of the reaction, concentrated hydrochloric acid was added to the reaction mixture and the mixture was extracted 3 times with 200 ml chloroform. The results of a gas chromatography analysis performed on the extract and the collected gas indicated that 4,4,4-trifluorobutyliodide was converted at 86.8% conversion rate, and the selectivity for 4,4,4-trifluorobutanol, 4,4,4-trifluoro-1-butene, and bis(4,4,4-trifluorobutyl)ether were 44.9%, 50.2%, and 4.9%, respectively.

INDUSTRIAL APPLICABILITY

According to the method of the present invention, fluorinated alcohols can be produced from fluorinated alkyl halides at high yield and at high selectivity in a single-step reaction. Furthermore, this method eliminates the need for heavy metals and other toxic compounds that are difficult to handle or process.

What is claimed is:

1. A method for producing a fluorinated alcohol represented by the following general formula (2):

$$Rf(A)OH \quad (2)$$

wherein Rf represents a perfluoroalkyl group having 1 to 10 carbon atoms; and A represents a straight-chained or branched saturated hydrocarbon group having 3 to 10 carbon atoms, the method comprising the step of:

allowing a fluorinated alkyl halide represented by the following general formula (1) to react with an alkali metal salt of 4-hydroxybutyrate in a gamma-butyrolactone solvent:

$$Rf(A)X \quad (1)$$

wherein Rf and A are as defined above; and X represents a halogen atom.

2. The method according to claim 1, wherein the reaction is allowed to proceed at a temperature of 120° C. or below until the amount of the remaining fluorinated alkyl halide becomes 10% or less and is subsequently carried out at a temperature of 120° C. or above.

3. The method according to claim 1, wherein the alkali metal salt of 4-hydroxybutyrate is a potassium salt of 4-hydroxybutyrate.

4. The method according to claim 1, wherein the fluorinated alkyl halide is 4,4,4-trifluorobutylhalide and the fluorinated alcohol is 4,4,4-trifluorobutanol.

5. The method according claim 1, wherein the resulting fluorinated alcohol is distilled out to facilitate the conversion of 4-hydroxybutyric acid ester, an intermediate present in the reaction mixture, into the fluorinated alcohol and the gamma-butyrolactone.

* * * * *